(12) United States Patent
Ajagbe

(10) Patent No.: US 6,875,200 B1
(45) Date of Patent: Apr. 5, 2005

(54) BANDAGE FOR PROTECTION OF SKIN SURROUNDING AN UMBILICAL CORD STUMP

(76) Inventor: Olubunmi J. Ajagbe, 20303 Oyster Bay Ter., Gaithersburg, MD (US) 20886

(*) Notice: Subject to any disclaimer, the term of this patent is extended or adjusted under 35 U.S.C. 154(b) by 92 days.

(21) Appl. No.: 10/339,852

(22) Filed: Jan. 10, 2003

(51) Int. Cl.[7] .......................... A61M 35/00; A61F 13/00
(52) U.S. Cl. ...................... 604/290; 604/289; 604/304; 604/307; 602/41; 602/54; 602/58
(58) Field of Search ...................... 602/41–59; 128/888, 128/889, 890, 893, 894; 604/304–308, 180; D24/127, 128, 189; 2/49.1, 49.4

(56) References Cited

U.S. PATENT DOCUMENTS

| | | | |
|---|---|---|---|
| 612,997 A | 10/1898 | Smith | 604/346 |
| 1,590,629 A | 6/1926 | Julius | 16/414 |
| 3,422,817 A | 1/1969 | Mishkin et al. | 128/846 |
| 5,370,627 A | * 12/1994 | Conway | 604/180 |
| 5,669,770 A | * 9/1997 | Fisher et al. | 433/137 |
| 5,672,056 A | * 9/1997 | Fisher et al. | 433/137 |
| 5,968,000 A | 10/1999 | Harrison et al. | 602/41 |
| 6,571,395 B1 | * 6/2003 | Korkor | 2/45 |

FOREIGN PATENT DOCUMENTS

| | | | | |
|---|---|---|---|---|
| BR | 9400353 A | * 10/1995 | | A61F/13/02 |
| FR | 2671270 A1 | * 7/1992 | | A41B/13/10 |

* cited by examiner

Primary Examiner—Kim M. Lewis
(74) Attorney, Agent, or Firm—Goldstein Law Offices, P.C.

(57) ABSTRACT

A bandage for protecting the skin of an infant's stomach surrounding an umbilical cord stump from the irritating effects of medicinal solutions. The bandage is substantially flat and has an absorbent upper surface, a substantially nonabsorbent lower surface, and a circular central cutout wherefrom the umbilical cord stump may be extended. The bandage has a flap closure portion comprising a bottom flap and an overlapping top flap. The top flap has adhesive on its lower surface whereby the top flap maybe attached to the bottom flap. In use, the bandage is placed on the infant's stomach with the umbilical cord stump extending therefrom. Then, the lower surface of the top flap is attached to the underlying bottom flap. With the protective bandage in place, a variety of solutions may be applied to the umbilical cord stump without irritating the sensitive skin of the infant's stomach.

1 Claim, 2 Drawing Sheets

US 6,875,200 B1

BANDAGE FOR PROTECTION OF SKIN SURROUNDING AN UMBILICAL CORD STUMP

BACKGROUND OF THE INVENTION

1. Field of the Invention

The invention generally relates to bandages, and in particular it relates to bandages for protecting skin surrounding an umbilical cord stump.

2. Description of the Related Art

Prior to birth, an infant receives oxygen and nutrients via an umbilical cord. After birth, the umbilical cord is no longer necessary and it is clamped and cut by a doctor or nurse. The remaining portion of the umbilical cord, the umbilical cord stump, typically falls away within two weeks. However, until that time, the umbilical cord stump must be cared for. The umbilical cord stump may be treated with a variety of solutions, including alcohol, iodine, or antibacterial preparations, to prevent infections and to "dry out" the umbilical cord during this interim period. However, these solutions may dry out or irritate the tender skin of the infant's stomach surrounding the umbilical cord stump. Consequently, there is a need for a bandage which covers and protects the infant's skin in this area while allowing the umbilical cord stump to extend from the bandage so that various solutions may be applied to the umbilical cord stump.

A wide variety of bandages have been devised for protection of areas of skin. U.S. Pat. No. 612,997 to Smith appears to show a bandage for an umbilical cord. However, Smith appears to contemplate a bandage which covers and encloses the umbilical cord. Accordingly, Smith is useless for protection of the sensitive skin which surrounds the umbilical cord stump.

U.S. Pat. No. 3,422,817 to Mishkin appears to show a bandage with a central opening with overlapping portions, whereby the bandage may be fitted over a tracheotomy tube. However, Mishkin is concerned with protection of the wound site surrounding a tracheotomy tube and accordingly, does not provide a bandage which is useful for protection of the sensitive skin surrounding the umbilical cord stump.

U.S. Pat. No. 5,968,000 to Harrison appears to show a bandage for covering a wound site caused by insertion of a catheter into a patient. However, Harrison is concerned primarily with covering a circular wound site with a bandage which has a handle into which a catheter may be received. Accordingly, Harrison does not provide a bandage which protects an area of skin from solutions which are topically applied to the surrounding skin.

While these units may be suitable for the particular purpose employed, or for general use, they would not be as suitable for the purposes of the present invention as disclosed hereafter.

SUMMARY OF THE INVENTION

It is an object of the invention to produce a bandage which protects the sensitive skin of an infant's stomach surrounding an umbilical cord stump from a variety of solutions which are topically applied to the umbilical cord stump. Accordingly, the bandage has a central cutout, thereby permitting the bandage to be extended over the umbilical cord stump for protection of skin surrounding the stump.

It is another object of the invention to produce a bandage which may be secured in place around the umbilical cord stump. Accordingly, the bandage has a flap closure portion comprising a bottom flap and an overlapping top flap, and has adhesive on the lower surface of the top flap, whereby the top flap may be secured to the bottom flap.

It is yet another object of the invention to produce a bandage which is sterile. Accordingly, the bandage may be individually wrapped in sterile packaging, thereby insuring that each bandage is free from bacteria.

It is still another object of the invention to produce a bandage which may be placed comfortably against the skin of an infant to absorb the solutions which are used to wash the umbilical cord stump. Accordingly, the bandage has a soft and absorbent upper surface which does not contact the skin and a soft nonabsorbent lower surface which is in contact with the skin and will not readily absorb liquid, thus protecting the infant's skin.

It is an additional object of the invention to produce a bandage which is suitable for infants regardless of their size. Accordingly, the bandage is provided in two sizes, whereby the larger size is used for larger infants and the smaller size is used for smaller infants.

It is another object of the invention to produce a bandage which may be used by parents and caretakers as well as by hospitals and birthing centers. Accordingly, the bandage is simple to apply and can be used even by individuals who are not trained in the health care area.

It is additionally an object of the invention to produce a bandage which is aesthetically pleasing. Accordingly, the bandage is provided in a variety of designs and pastel colors.

The invention is a bandage for protecting the skin of an infant's stomach surrounding an umbilical cord stump from the irritating effects of medicinal solutions which are applied to the umbilical cord stump. The bandage is substantially flat and has an absorbent upper surface, a substantially nonabsorbent lower surface, and a circular central cutout wherefrom the umbilical cord stump may be extended. The bandage has a flap closure portion comprising a bottom flap and an overlapping top flap. The top flap has adhesive on its lower surface whereby the top flap may be attached to the bottom flap. In use, the bandage is placed on the infant's stomach with the umbilical cord stump extending therefrom. Then, the lower surface of the top flap is attached to the underlying bottom flap. With the protective bandage in place, a variety of solutions may be applied to the umbilical cord stump without irritating the sensitive skin of the infant's stomach.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
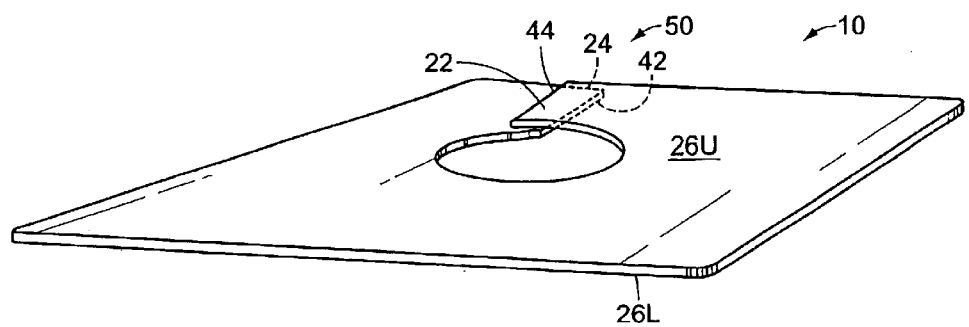
FIG. 1 is a perspective view of the bandage wherein the bandage is substantially rectangular in shape.
Figure 2:
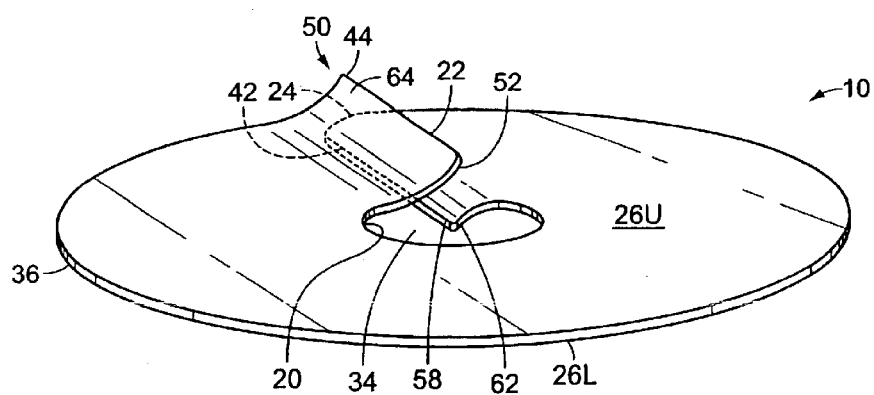
FIG. 2 is a perspective view of the bandage wherein the bandage is substantially circular in shape.

FIG. 1 illustrates a perspective view of the bandage 10 wherein the bandage 10 is rectangular in shape. FIG. 2 illustrates a perspective view wherein the bandage is circular in shape. Both designs are structurally analogous. Hence, a detailed description of the circular design in FIG. 2 will suffice.

The bandage 10 shown in FIG. 2 is substantially circular, having an upper surface 26U and a lower surface 26L, an outer peripheral edge 36, and a circular central cutout 34 defined by an inner peripheral edge 20 for accommodating an umbilical cold stump. The bandage 10 has a flap closure portion 50 comprising a bottom flap 24 and an overlapping top flap 22. The bottom flap 24 has an absorbent upper surface 58, a nonabsorbent lower surface 62, and a lower slit 42 which extends from the outer peripheral edge 36 to the inner peripheral edge 20. Analogously, the top flap 22 also has an upper surface 64, a lower surface 52, and an upper slit 44 which extends from the outer peripheral edge 36 to the inner peripheral edge 20. However, both the upper surface 64 and the lower surface 52 of the top flap 22 are constructed from absorbent material, and the lower surface 52 further comprises an adhesive, whereby the top flap 22 may be fastened to the upper surface 58 of the bottom flap 24. The top flap 22 is provided with a self-adhesive backing on the lower surface 52 which may be peeled off so that the top flap 22 can be attached to the bottom flap 24. Both the lower slit 42 and the upper slit 44 extend fully from the upper surface 26U to the lower surface 26L of the bandage 10. The lower surfaces 26L, 62, and 52 are constructed from nonabsorbent hypoallergenic nylon and are in contact with the skin of the infant. The upper surfaces 26U, 64, and 58 are preferably constructed from light gauze or like material and are not in contact with the skin of the infant's stomach while the bandage 10 is being used.

Figure 3:
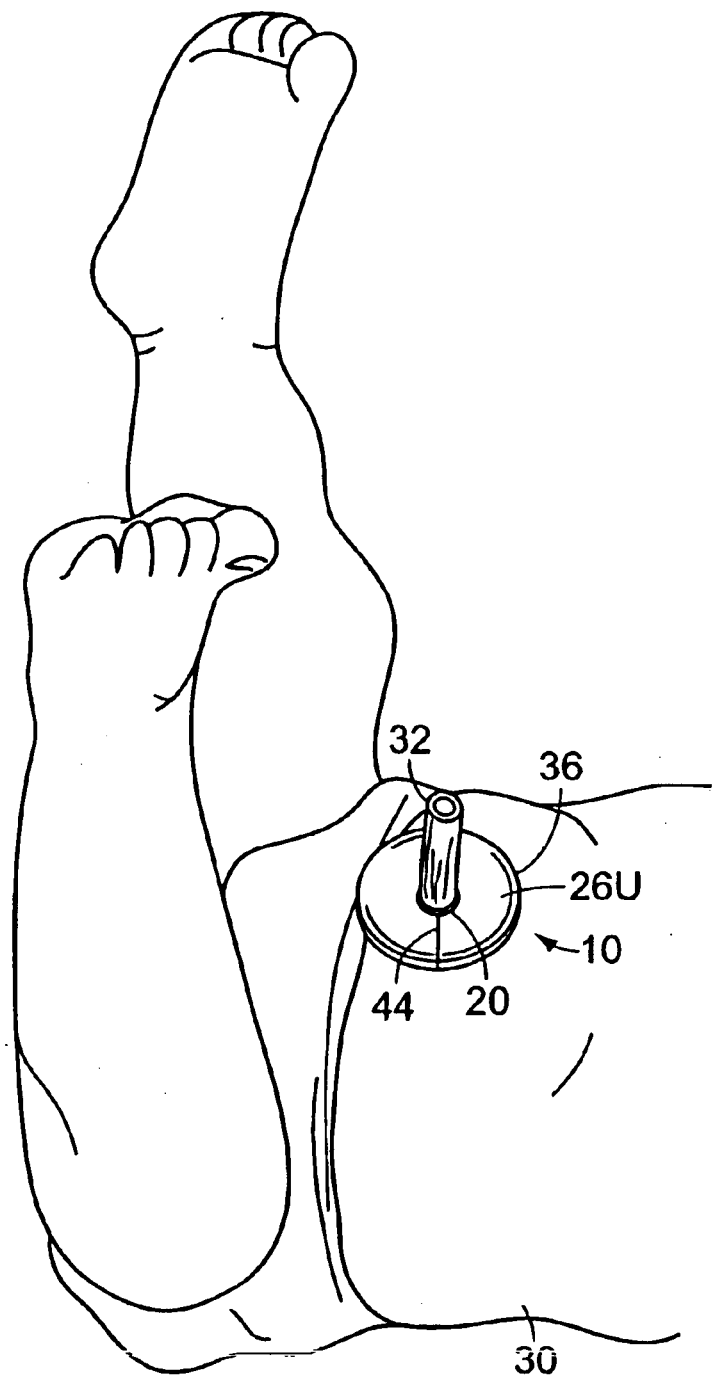
FIG. 3 is a perspective view of the bandage protecting the skin of an infant which surrounds an umbilical cord stump.

FIG. 3 illustrates a perspective view of the bandage 10 while being utilized to protect the skin of an infant 30 which surrounds the umbilical cord stump 32. The upper surface 26U of the bandage 10 is visible, as is the upper slit 44, the outer peripheral edge 36, and the inner peripheral edge 20.

In use, a user selects a size of the bandage 10 that best fits the infant 30. Then, any clothes which cover the umbilical cord stump 32 are removed. The infant 30 is then laid on its back. The user then holds the bandage 10 with both hands, with one hand on each side of the flap closure portion 50. The flap closure portion 50 is then gently pulled apart. The self-adhesive backing on the lower surface 52 of the top flap 22 is then peeled off and the top flap 22 is attached to the bottom flap 24. With the soft, absorbent upper surface 26U of the bandage 10 oriented upward, a treatment solution such as alcohol or iodine may be safely applied to the umbilical cord stump 32. After use, the bandage 10 is removed by peeling the top flap 22 from the bottom flap 24. The bandage 10 is then discarded.

In conclusion, herein is presented a bandage for protecting the sensitive skin surrounding an umbilical cord stump from the irritating effects of a variety of solutions which are used to bathe the umbilical cord. The invention is illustrated by example in the drawing figures, and throughout the written description. It should be understood that numerous variations are possible, while adhering to the inventive concept. Such variations are contemplated as being a part of the present invention.

What is claimed is:

1. A method of using a bandage for protecting the skin of an infant surrounding the stump of an umbilical cord by a user having two arms each having a hand, said bandage comprising an upper surface constructed from absorbent material, a lower surface constructed from nonabsorbent material, an outer peripheral edge, a circular central cutout defined by an inner peripheral edge for accommodating an umbilical cord, a flap closure portion comprising a bottom flap and an overlapping top flap, said bottom flap having an absorbent upper surface, a nonabsorbent lower surface, and a lower slit extending from the outer peripheral edge to the inner peripheral edge, said top flap also having an upper surface, a lower surface, and an upper slit extending from the outer peripheral edge to the inner peripheral edge, wherein both the lower slit and the upper slit extend fully from the upper surface to the lower surface of the bandage, wherein both the upper surface and the lower surface of the top flap are constructed from absorbent material, and wherein the lower surface of the top flap further comprises an adhesive and a self-adhesive backing, whereby the lower surface of the top flap may be fastened to the upper surface of the bottom flap, comprising the steps of:

a) removing any clothes of the infant which cover the umbilical cord stump;
   b) laying the infant on its back;
   c) holding the bandage with both hands by the user, with one hand on each side of the flap closure portion;
   d) pulling apart the flap closure portion by the user;
   e) peeling off the self-adhesive backing on the lower surface of the top flap by the user;
   f) placing the lower surface of the bandage against the skin of the baby which surrounds the umbilical cord stump with the stump extending through the circular central cutout;
   g) attaching the top flap to the bottom flap by pressing the top flap gently onto the bottom flap;
   h) applying a treatment solution to the umbilical cord stump;
   i) removing the bandage after use after peeling apart the top flap from the bottom flap; and
   j) discarding the bandage.

* * * * *